(12) United States Patent
Mäder et al.

(10) Patent No.: US 8,904,846 B2
(45) Date of Patent: Dec. 9, 2014

(54) DEVICE AND METHOD FOR PROVIDING A STENT FOR IMPLANTATION

(75) Inventors: Armin W. Mäder, Richterswil (CH); Arik Zucker, Zürich (CH)

(73) Assignee: Qvanteq AG (CH)

( * ) Notice: Subject to any disclaimer, the term of this patent is extended or adjusted under 35 U.S.C. 154(b) by 971 days.

(21) Appl. No.: 13/002,380

(22) PCT Filed: Jun. 9, 2009

(86) PCT No.: PCT/CH2009/000189
§ 371 (c)(1),
(2), (4) Date: Feb. 23, 2011

(87) PCT Pub. No.: WO2010/000079
PCT Pub. Date: Jan. 7, 2010

(65) Prior Publication Data
US 2011/0152995 A1 Jun. 23, 2011

(30) Foreign Application Priority Data
Jul. 4, 2008 (CH) ........................................ 1036/08

(51) Int. Cl.
*B21D 41/00* (2006.01)
*A61F 2/82* (2013.01)
*A61F 2/00* (2006.01)
*A61F 2/95* (2013.01)

(52) U.S. Cl.
CPC ................. *A61F 2/82* (2013.01); *A61F 2/0095* (2013.01); *A61F 2002/9522* (2013.01); *A61F 2250/0092* (2013.01)
USPC .................... 72/402; 72/38; 72/39; 72/370.25

(58) Field of Classification Search
CPC ........ B21D 39/04; B21D 41/00; B21D 41/04; A61F 2/06; A61F 2/82
USPC ................ 72/38, 39, 40, 41, 42, 401, 370.13, 72/370.25, 402; 29/237, 282, 283.5; 53/453, 559; 623/1.11, 1.15
See application file for complete search history.

(56) References Cited

U.S. PATENT DOCUMENTS 4,292,095 A * 9/1981 Schlinsog .................. 148/243
6,141,855 A 11/2000 Morales
(Continued)

FOREIGN PATENT DOCUMENTS

JP 2002525167 8/2002
JP 2005527276 9/2005
(Continued)

OTHER PUBLICATIONS

International Search Report dated Aug. 31, 2009, issued in corresponding international application No. PCT/CH2009/000189.

*Primary Examiner* — Edward Tolan
(74) *Attorney, Agent, or Firm* — Ostrolenk Faber LLP

(57) ABSTRACT

A device and a method for providing a stent for implantation into a body lumen are provided, wherein the stent (3) has a proximal end (31) and a distal end (32), between which a stent lumen having a compressible diameter d extends. The device comprises a crimping apparatus (4), having elements (40) which are disposed about an axis and can be moved at least partially relative to each other radially to the axis, and an activator (42) for actuating the crimping apparatus (4). The elements (40) of the crimping apparatus comprise the stent (3) and can be moved radially by means of the activator (42) from a widened position, in which the stent (3) is not crimped, into a closed position, in which the diameter d of the stent (3) is compressed. According to the invention, a storage compartment comprising an inert medium or an inert filling is provided, which forms a jacket in which the stent (3) is stored in an inert manner at least the majority of the time, while the elements (40) enclose the stent (3) and are moved from the widened position into the closed position. The inert jacket can be interrupted during compression of the stent.

20 Claims, 16 Drawing Sheets

(56) References Cited

U.S. PATENT DOCUMENTS

| | | |
|---|---|---|
| 6,968,607 B2 | 11/2005 | Motsenbocker |
| 7,225,518 B2 * | 6/2007 | Eidenschink et al. ....... 29/283.5 |
| 7,316,148 B2 * | 1/2008 | Asmus et al. ................... 72/402 |
| 7,487,579 B2 * | 2/2009 | Eidenschink et al. .......... 29/515 |
| 2003/0187493 A1 * | 10/2003 | Campbell et al. ............ 623/1.11 |
| 2006/0183383 A1 | 8/2006 | Asmus et al. |
| 2007/0288085 A1 | 12/2007 | Furst |
| 2008/0072653 A1 | 3/2008 | Gillick et al. |
| 2008/0086198 A1 | 4/2008 | Owens et al. |

FOREIGN PATENT DOCUMENTS

| | | |
|---|---|---|
| WO | WO 2006/050425 A2 | 5/2006 |
| WO | WO 2006/086709 A1 | 8/2006 |

* cited by examiner

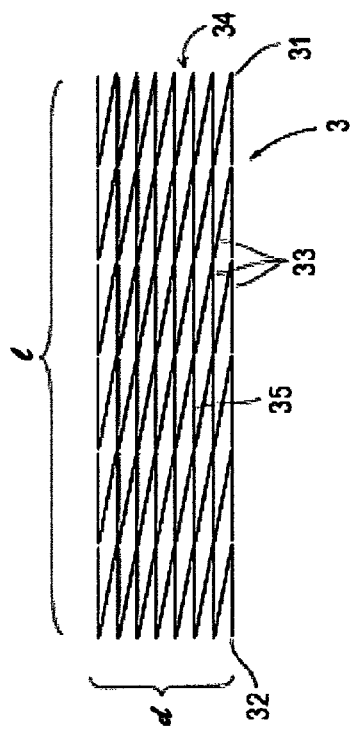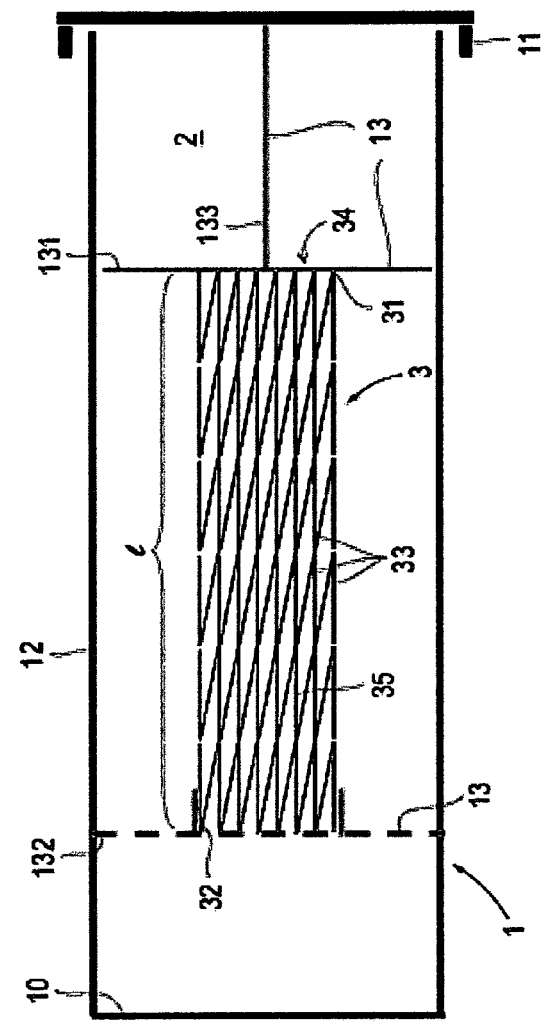

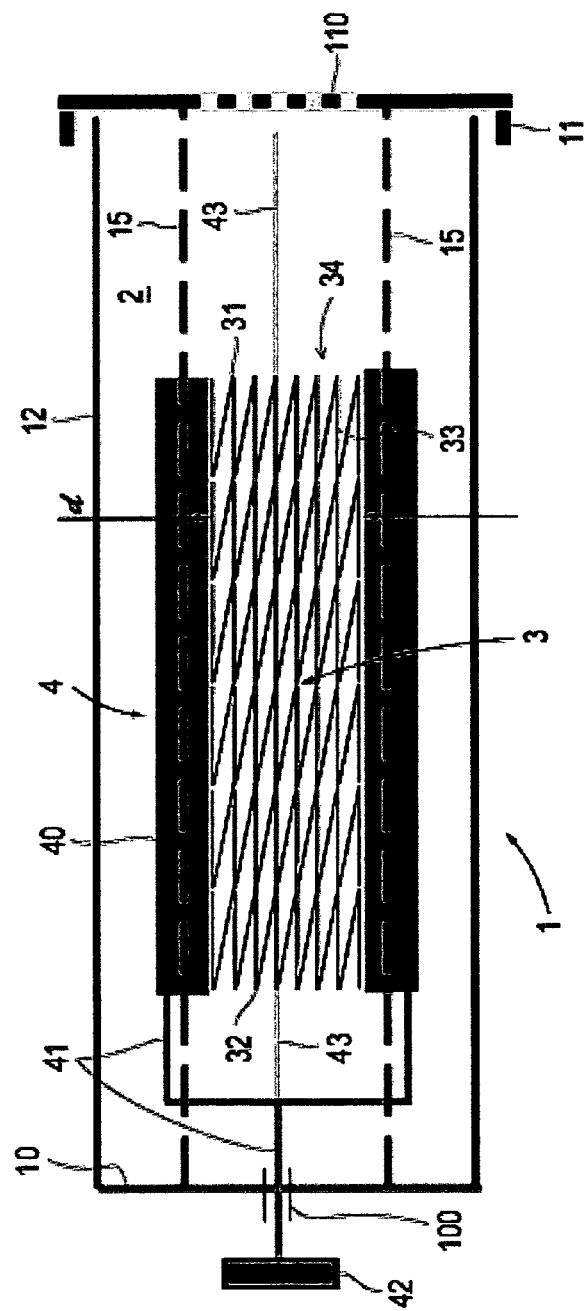

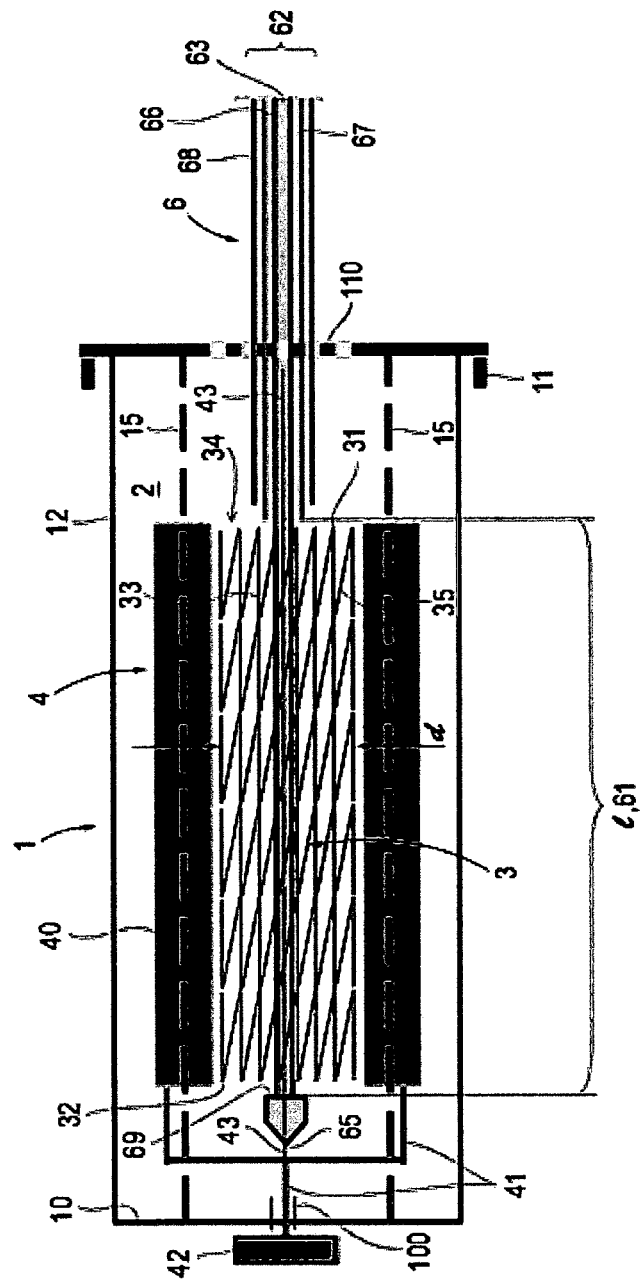

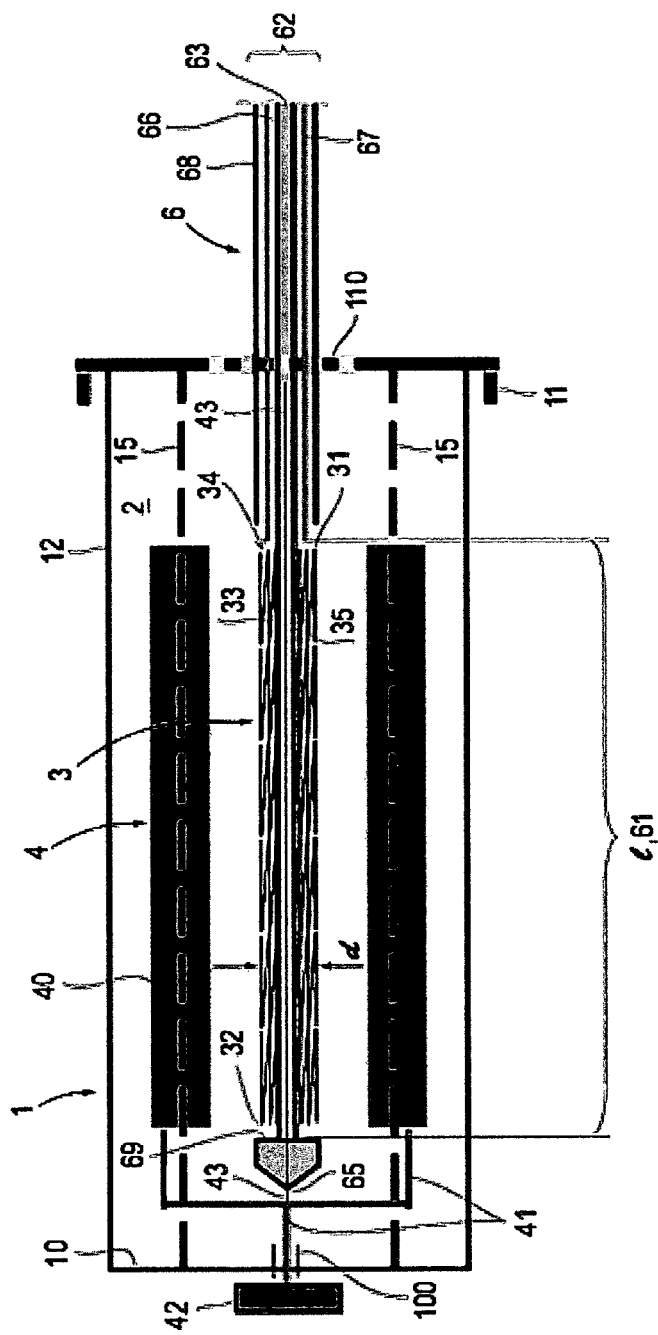

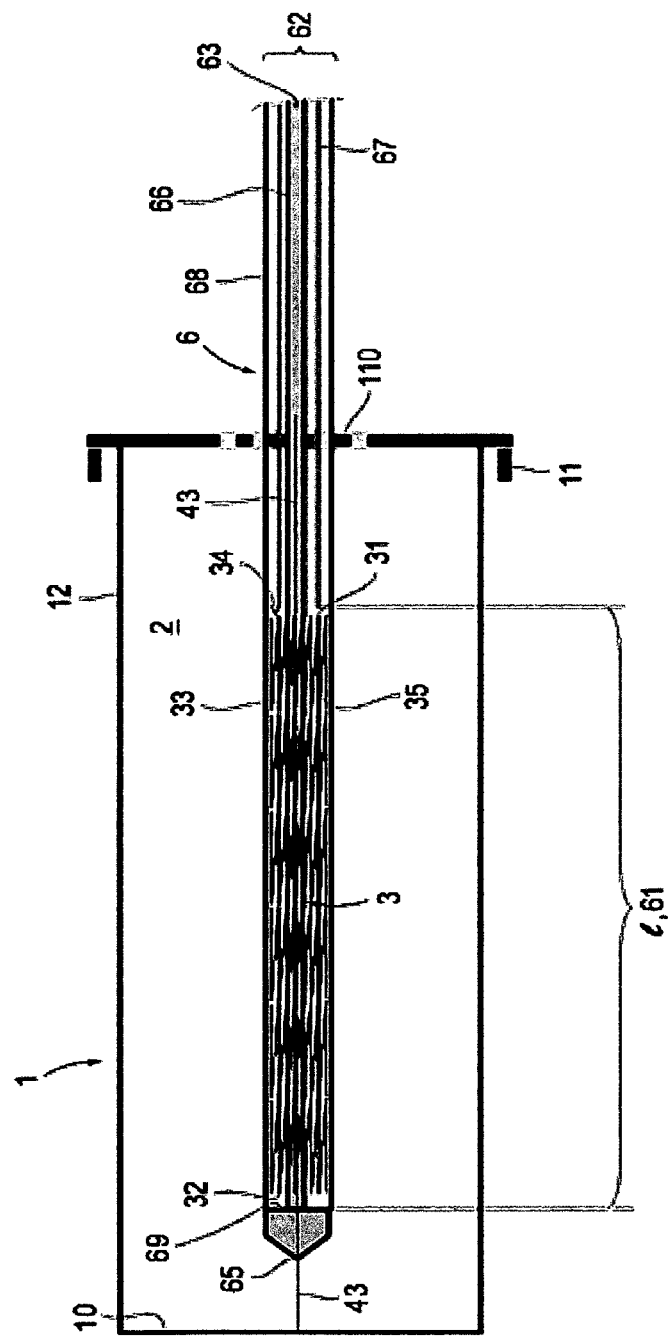

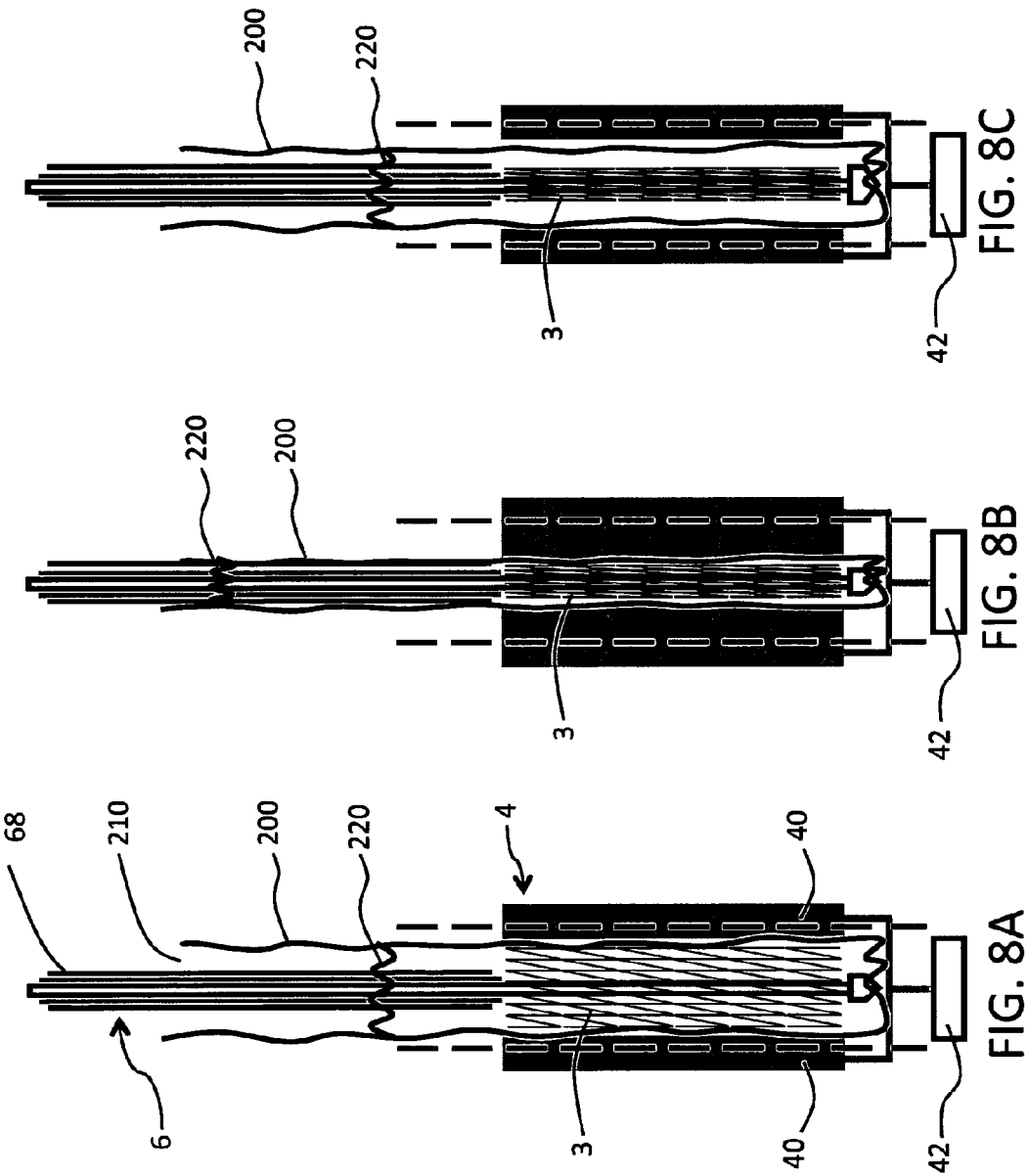

DEVICE AND METHOD FOR PROVIDING A STENT FOR IMPLANTATION

CROSS REFERENCE TO RELATED APPLICATIONS

The present application is a 35 U.S.C. §371 National Phase conversion of PCT/CH2009/000189, filed Jun. 9, 2009, which claims benefit of Swiss Application No. 1036/08, filed Jul. 4, 2008, the disclosure of which is incorporated herein by reference. The PCT International Application was published in the German language.

BACKGROUND

1. Field of the Disclosure

The present invention relates to a device for providing a stent for implantation into a body lumen, more particularly for compressing a balloon-expanding stent onto a balloon catheter or for compressing a self-expanding stent to be inserted into a tube catheter, and to a method for providing the stent for an implantation.

2. Related Art

By way of example, stents are used as a medical implant for treating lesions in blood vessels. In general, a stent has a multiplicity of webs that together form a tubular shape. The stent length and, as a passage, the stent lumen with a compressible diameter extend between a proximal and a distal end. The stent assumes an expanded diameter in the dilated or released state, for example for supporting the blood vessel. The stent surface can be embodied in a hydrophilic fashion to promote hemocompatibility.

A special field of application is the vessel dilation in the field of percutaneous transluminal angioplasty, also including cardiovascular intervention. Such stents are together with a catheter, which is provided specially for this, inserted into the human body through a minimal opening, e.g. by puncturing an artery in the region of the thigh, and are moved up to the lesion, i.e. the vessel restriction to be treated, and are dilated there. Whereas the stent remains in the dilated blood vessel and supports the latter from the inside, the catheter is removed from the body. The flow of blood through the dilated and supported blood vessel is once again ensured. This procedure is carried out with the aid of instantaneous X-ray recordings, which on a monitor display both the blood vessels and the instruments inserted into the body.

Another special field of application is the treatment of aneurysms, i.e. expanded blood vessels. In this treatment, a stent graft—consisting of a supporting mesh and a cover—is inserted into the aneurysm in order once again to ensure the conventional blood flow. Furthermore, a stent can also comprise further functional elements, such as closure elements for closing a lumen, valve-replacement elements, etc., as known in the prior art.

Moreover, stents in the prior art are widely used in a multiplicity of additional medical applications. A distinction is substantially made between balloon-expanding and self-expanding stents. Prior to implantation, balloon-expanding stents are applied to a non-expanded balloon. To this end, the stent is, for example, compressed to a smaller diameter over the balloon and inserted into the body together with the balloon. The balloon is expanded at the treatment site, e.g. at a lesion or a vessel valve, such that it dilates the stent. The balloon may subsequently be removed from the body. By way of example, self-expanding stents consist of a metal with memory effect. They can be compressed against their elastic force in order to be inserted into a body lumen and can be inserted into a supply catheter. They are released from the catheter at the treatment site and jump back to their expanded state.

However, the metallic stents implanted into blood vessels harbor certain risks for the patient. Inter alia, thromboses can form at the structures of the stent. Combined with medicaments administered to the patient after the implantation, the occurrences of thromboses in the case of bare metal stents (BMS) could be reduced to less than 1% within the first 10 days. Nevertheless, this is one of the most-feared complications, particularly in the case of the coronary intervention.

A property of the stent that is desired by medical practitioners is the rapid growing in thereof, the so-called reendothelialization. The latter is of the utmost importance for the success of the stent therapy because the cells in this endothelial layer form essential antithrombotic factors. However, as long as the stent has not grown in, and the structures thereof are subjected to the blood flow, it is of the utmost importance to provide an antithrombotic stent surface.

It is well-known that stents with hydrophilic surface properties have a much higher hemocompatibility, i.e. a much lower thrombogenicity. Substances are applied onto the stent surface, for example by means of coating methods, in order to increase the hydrophilicity on the stent surfaces.

By way of example, possible coating methods include "chemical vapor deposition" (CVD) or "physical vapor deposition" (PVD), by means of which materials, e.g. polymers or metals with defined layer thicknesses, are applied onto the stent surface. It was found that in the case of a polymer-coated BMS, the thrombocyte formation was reduced from 85% (BMS) to 20% (polymer-coated BMS) as a result of the increased hydrophilic properties of the surface.

The stent surface is coated with an active substance in a further application. By way of example, glucocorticoids, cytostatic agents, immunomodulators or antiproliferative agents are used as active substances. The substances, and hence the medical active ingredient, are successively released after the stent is implanted into the body.

It is common to all stents that these need to have a smaller diameter for being introduced into a body lumen than when they carry out their function in the body. In general, the producer pre-fits the stents on a catheter and packages them. However, a stent may also be compressed only just before said stent is inserted into the body lumen. In conventional methods for providing a stent for implantation, the stent is usually subjected to the necessary surface treatment in an expanded or semi-expanded state and subsequently compressed to a smaller diameter, which is suitable for the insertion into the body of a patient, by means of a crimping apparatus.

By way of example, U.S. Pat. No. 6,968,607 B2 discloses a crimping apparatus consisting of a plurality of crimping segments. The ends of the crimping segments are attached to a drum along a circle and can be pivoted about a pivot, which is at a distance from the attachment point. The other end of the crimping segments can be pivoted toward the center of the circle by rotating the drum. In the pivoted-open state, the crimping segments form a central opening therebetween, into which a stent can be inserted such that the segments encompass the stent. When the segments are pivoted toward the center of the circle, the central opening is reduced and the individual segments press against the external circumference of the stent from all sides such that the latter is compressed. The drum can be rotated by means of an actuation lever. The stents are fed to the crimping apparatus through an input and output opening and are removed in the crimped state.

Similar crimping apparatuses, for example with an integrated device for tempering the stent during the crimping process, or for example with an integrated device that provides the stent with an envelope during the compression, are known from US 2008/0072653 A1 and WO 2006/050425 A2.

In another crimping apparatus according to U.S. Pat. No. 6,141,855, a stent is encompassed by a Mylar film. The ends of the film are guided through a slit in a solid plate, and so the film forms a loop with a variable diameter, within which the stent is arranged. In order to compress the stent, the ends of the film are pulled such that the diameter of the loop is reduced and the stent is pressed together by the film. By way of example, this crimping apparatus can be used to crimp the stent onto e.g. the balloon of a balloon catheter.

When a stent for implantation is provided using crimping apparatuses from the prior art, the stents are generally subjected to the surrounding environment in an unprotected fashion during the insertion into the crimping apparatus and are contacted by the elements of the crimping apparatus. In the process, they are subjected to contamination by e.g. reagents situated in the air, such as hydrocarbon molecules, which can adversely affect a hydrophilic surface of a stent or an active substance on the stent. The stent surface can also be contaminated by residues on the elements of the crimping apparatus. Furthermore, there is the risk of undesired contamination of or change in the stent surface when transferring a crimped stent from a conventional crimping apparatus.

SUMMARY

It is an object of the present invention to propose a device and a method for providing a stent for implantation in a body volume, which prevent an adverse effect on or a contamination of the stent, more particularly the stent surface, during the compression of the stent, simplify the handling of the stent during the preparation for the implantation and increase the safety against undesired interactions of the stent surface before the implantation. Furthermore, a packaging for storing and transporting initially uncrimped stents should be presented, which stents are suitable for use in means for mounting the stent on a catheter, wherein, in particular, a hydrophilic property of the stent surface is maintained.

This object is achieved by the invention by means of a device and a method according to claims 1 and 18. Advantageous embodiments and different exemplary embodiments are described in the dependent claims.

According to the present invention, provision is made for a device for providing a stent for implantation into a body lumen. The device is provided for a stent, which has a proximal end and a distal end, wherein a stent lumen with a compressible diameter extends between the ends. The device comprises a crimping apparatus with elements, which are arranged around an axis and can at least in part move radially with respect to the axis relative to one another, as a result of which the free space enclosed by the elements is reduced. Furthermore, the device comprises an activator for actuating the crimping apparatus. The elements of the crimping apparatus encompass the stent and can be moved in the radial direction from a dilated position, in which the stent is uncrimped or uncompressed, into a closed position, in which the stent has a compressed diameter, by means of the activator. In the dilated position of the elements, the free space enclosed thereby has a diameter which is at least big enough to house the stent in this space, when said stent is in an expanded state. In the closed position of the elements, the elements have been moved so far radially inward that the free space has been reduced to a diameter that corresponds to the diameter provided for a compressed or crimped stent.

The crimping apparatus elements can be embodied as pivotable jaws or as segments, which are arranged in an annular fashion around an axis and can move in the direction of the axis. However, the crimping apparatus may also have a loop as an element, which loop can e.g. be pulled together and thus compress a stent situated within the loop. Furthermore, a shrink tubing can be provided as moveable element of the crimping apparatus, into which the stent is inserted and which subsequently shrinks due to heating. Finally, threads can also be applied to the stent such that the stent is compressed when the threads are pulled. Such crimping apparatuses are known from the prior art.

A storage space consisting of an inert medium or with an inert filling is provided in the device according to the invention, which storage space forms an envelope in which the stent is stored for most of the time in an inert fashion while the elements encompass the stent and can be moved from the dilated position into the closed position. Thus, the storage space is at least in part provided in the free space enclosed by the elements of the crimping apparatus, but it can also extend radially beyond the elements. Hence, the crimping apparatus can wholly or partly be arranged within the storage space. By way of example, the moveable elements of the crimping apparatus can be provided within the storage space. Parts of a drive for the moveable elements, e.g. a driveshaft, can at least in part also be housed within the storage space in the inert surroundings. Alternatively, the crimping apparatus may also be arranged completely outside of the storage space such that it acts on the stent through a wall of the storage space. The activator for the crimping apparatus is preferably provided outside of the storage space.

According to the invention, preferably the entire contents of the storage space are inert and filled with the inert filling. By way of example, the inert filling of the storage space can be provided by an inert gas, such as argon or nitrogen, or water, more particularly water with water for injection quality (WFI quality), or by a gel. Within the scope of the invention, a medium or a filling should be considered inert if the purity or cleanliness of the surface of the stent is not changed or adversely affected by the medium or the filling. Thus there is no reaction between the stent and the medium or the filling. Thus, a vacuum in the storage space should also be understood to be an inert filling. Hence, in the case of sterile surfaces, the killed pyrogenic substances, adhering to the surface after the sterilization, also remain on the surface in the inert medium or in the inert filling. In the case of hydrophilized surfaces, no new reagents can be deposited on the cleaned or sanitized surface, and so no recontamination is possible.

The storage space consisting of an inert medium or with an inert filling forms an envelope for the stent or the surface of the stent. The envelope can e.g. also be produced by a gas flow, which streams around the stent on all sides, and so the surface of said stent is situated within a gas cloud and is covered by the gas. By way of example, the gas can flow along the axis of the crimping apparatus and can be guided through the free space between the moveable elements. Thus, the storage space is delimited by the edge of the gas flow. A wetting film on the surface of the stent can also serve as an envelope. The stent may be stored e.g. in WFI water. When the stent is removed from the water, a film remains on the surface of the stent, and so the latter remains wetted. The wetting film allows the stent to be stored in an inert fashion. In this case the storage space is delimited by the surface of the wetting film.

However, any container or a malleable bag, whose dimensions are sufficient to house the uncompressed stent and whose wall is sufficiently tight to keep the inert medium in the inner space, can also serve as storage space. By way of example, the storage space may be provided by a container filled with an inert medium that is heavier than air, such as argon or water with WFI quality. In this case, the container need not be sealed toward the top because the heavy medium does not escape the container on its own accord. Hence the stent or else the crimping apparatus can easily be introduced into the container.

In a provision device according to the invention, the stent is stored in an inert fashion for most of the time, preferably during the entire time interval, during which time interval the elements encompass the stent and are moved from the dilated position into the closed position. The time interval is determined by the time required by the crimping apparatus to bring the stent from an uncompressed into a compressed state by moving the crimping elements. The envelope of the stent with the inert medium or the inert filling can be broken during this process over a period of time during which there is no significant recontamination of the stent surface.

A recontamination is not significant as long as it does not assume an extent on the surface of the stent that is relevant to the clinical success. The duration of the period of time of the break without there being significant recontamination depends on, inter alia, the type of material used by the stent and the roughness of the surface thereof. By way of example, a nitinol stent can remain without an inert envelope for a plurality of minutes without there being relevant contamination, for example as a result of depositing carbon chains. Hence a stent can remain in the free atmosphere for a number of minutes without there being a significant recontamination.

Hence, the stent can, for example, be cleaned outside of the provision device according to the invention, be kept in an inert fashion in the cleaned state and be removed from this inert storage in order to be inserted into the provision device. In the provision device according to the invention, the stent can be introduced into the storage space in which it is once again stored in an inert fashion. The period of time of the break in the inert envelope of the stent between the inert storage after cleaning and the inert storage in the provision device should be so short that there is no significant recontamination, as explained above. The same holds true for removing the stent from the provision device after the stent has been compressed. In principle the stent can also be compressed during the period of time of the break, provided the latter is so short that there is no onset of recontamination, as explained in more detail below.

The storage space can be fixedly provided in the provision device or arranged in a removable fashion. Thus, the storage space can e.g. be introduced into the device together with the stent, for example after the pretreatment of the stent surface in the storage space. By way of example, the stent is subjected to a treatment for cleaning the surface when it is within the storage space of the device, wherein the storage space can be within the provision device. By way of example, if a metallic stent is provided for the implantation, the stent surface of which should have a hydrophilic property, the molecular-chemical contaminants originating from the atmosphere, mainly hydrocarbons, can be significantly reduced on the surface by a suitable cleaning treatment, as a result of which, as a measure of the hydrophilicity, the contact angle of a water droplet situated on the surface is reduced compared to the contact angle before this treatment. The stent is stored in an inert fashion in the storage space in order to prevent natural recontamination from the atmosphere. Provided the treatment takes place outside of the provision device, the hydrophilized stent with the storage space may be inserted into the provision device. In principle, it is also feasible for a cleaning treatment to be carried out in a different container, preferably with an inert filling, as described above, and the stent is introduced into the storage space of the provision device after the treatment, provided there is no significant recontamination during the transfer.

It is also possible to remove the stent after the compression from the inert storage space of the provision device with the aid of a transfer vessel, wherein the transfer vessel itself may have an inert filling, preferably the same as provided in the storage space. The transfer vessel can be inserted into the storage space and hold the stent in its interior. Subsequently the transfer vessel and the stent are removed from the storage space and said transfer vessel carries along the stent accommodated in its interior. In the process the stent remains enveloped by the inert medium. The same holds true for inserting the stent into the storage space of the provision device. A screen or forceps may also be used as transportation means for the stent.

In the case of a device for providing a stent for implantation into a body lumen according to the present invention, the stent can be stored in an inert surrounding that protects it from recontamination or damage while the diameter thereof is reduced by the crimping apparatus and it is arranged in or on a catheter. More particularly, a hydrophilic surface property of the stent remains unchanged during the crimping process. This significantly reduces the danger of risks to the patient occurring during the implantation as a result of a contaminated stent.

In one embodiment of the present invention, a packaging, in which the stent is stored in an inert fashion, can be provided as the storage space. The packaging with the stent can be inserted into the provision device through an access until the elements of the crimping apparatus encompass the stent from outside of the packaging. Actuating the activator compresses the stent within the packaging by moving the elements from a dilated position into a closed position. The packaging preferably has a malleable wall. It is, for example, embodied as a bag. The wall can also be flexible such that it returns to its original shape after the stent has been compressed.

In another embodiment at least those elements of the crimping apparatus that act directly on the stent during the compression of the stent come to rest within the storage space and hence within the inert envelope of the stent. By way of example, pivotable segments or jaws, which are moved by a shaft, can be provided within the storage space. In this case a protective sheath may be provided between the stent and the elements. The protective sheath is preferably made of inert material, such as Teflon or ePTFE. The elements of the crimping apparatus may also have an inert surface, at least in those regions where they contact the stent. To this end the surface of the elements may be coated with e.g. Teflon. The elements can also at least in part consist of an inert material, such as Teflon or ePTFE. The surface of the elements preferably has a hydrophilic property. To this end, the elements can be subjected to a cleaning treatment, e.g. together with the stent, as described above. A hydrophilic property of the surface should be understood to mean that the surface has a contact angle of less than 90°. The degree of hydrophilicity depends on the type of material used in the elements.

The provision device can be used not only to compress the stent but also to attach the compressed stent in or on a catheter. To this end, at least a distal end of a catheter is provided within the storage space in order to hold the stent in the compressed state, wherein a balloon catheter or a tube catheter is assigned in a complementary fashion to a balloon-expanding or a self-expanding stent. Here the proximal end of the catheter can protrude out of the storage space through an access. However, the catheter can also be entirely housed within the storage space, for example if the storage space is provided by a transportation packaging. The uncompressed stent can already be pre-fitted or positioned on the catheter when it comes to rest in the crimping apparatus.

In one embodiment variant, the storage space consists of a packaging that consists of a container with a base and a cover. Here base and cover should be understood to mean two opposing sides or wall regions of the container. The base and/or the cover can be removed. The base and/or the cover have an access that can be opened, and so the stent can be removed from the packaging or the stent mounted on a catheter can be removed from the packaging together with the catheter.

The catheter has a tip at its distal end, and the proximal end of the catheter shaft opposite the tip protrudes out of the packaging through the access.

There is a passage in the base or in the cover for allowing a shaft to pass, which passage leads to the jaws of an integrated crimping apparatus toward the inside, into the packaging, and leads to an activator for actuating the crimping apparatus toward the outside. The access to be opened is present in the cover or in the base opposite the passage, which access serves to let a catheter pass. A guide mandrel extends through the crimping apparatus in the axial direction and it is used for stabilization and positioning purposes after it has been completely inserted into a guide wire lumen of the catheter. The access to be opened is advantageously made of e.g. a penetrable seal or a perforated material. Support elements for fixing the stent and/or the catheter and/or the crimping apparatus extend within the packaging.

The provision device can house the various apparatuses used to handle the stent in e.g. one housing. By way of example, the treatment apparatus and the crimping apparatus can be arranged within the housing. The housing has an opening for feeding or removing the stent or the storage space with the stent. Provision can also be made for two openings, one of which serves as a feed opening and the other serves as a removal opening. Provided the storage space is integrated into the housing, an apparatus for supplying the storage space with the inert filling is provided in the housing. The supply apparatus can be operated from outside of the housing, for example by means of inlet and outlet lines for the inert medium. If the storage space is arranged in the housing in a removable fashion, the inlet and outlet lines for the inert medium can be inserted into and removed from the housing together with the storage space.

According to a further aspect of the present invention, a method is proposed for providing a stent for implantation into a body lumen, which method is provided for a stent that has a proximal end and a distal end, with a stent lumen with a compressible diameter extending therebetween. In the provision method, the stent is stored in a storage space consisting of an inert medium or comprising an inert filling, which forms an envelope for the stent, and compressed using a crimping apparatus with moveable elements, which encompass the stent and are moved from a dilated position into a closed position. In the process, the stent remains in the inert envelope or a break in the inert envelope is provided over a period of time during which there is no significant contamination of a surface of the stent or no significant increase in a contact angle of a water droplet on the surface of the stent.

The break in the inert envelope can be brought about during the compression of the stent. By way of example, a gas flow of an inert gas, which forms the storage space for the stent, may be switched off for a short period of time. Or a stent wetted by an inert liquid may be left dry for a short period of time. According to the invention, the stent may also be compressed during the break provided the time required for the compression does not exceed the period of time for the break during which there is no significant contamination of the stent. In the process, the stent can be stored in a first inert medium or a first inert filling before the break in the inert envelope, and in a second inert medium or a second inert filling after the break in the inert envelope. Thus, the stent can be removed from a first inert envelope, be compressed by the crimping apparatus and subsequently be introduced into a second inert envelope.

The method according to the invention preferably provides for a cleaning treatment to be carried out before or during the inert storage of the stent, during which the molecular-chemical contaminants originating from the atmosphere, mainly hydrocarbons, are significantly reduced on the surface of the stent. As a result, as a measure of the hydrophilicity, there is a reduction in the contact angle of a water droplet situated on the surface compared to the contact angle before this treatment. Furthermore, the stent is preferably stored in a packaging with an inert filling after the compression. Finally, the stent may also be sterilized after the compression in order to kill microorganisms amongst others.

According to the method of the present invention, it is particularly advantageous for the stent to remain in the inert envelope during the progression of the method steps of the cleaning treatment, the storage, the compression, the packaging and optionally the sterilizing, or for provision to be made for a break in the inert envelope over a period of time during which there is no significant contamination on a surface of the stent or no significant increase in the contact angle of a water droplet on the surface of the stent. Hence, there is a substantially safe surrounding, in which the stent is not subjected to recontamination whilst all steps for providing the stent for implantation are carried out from the time of the cleaning treatment up to the packaging. Should a provision be made for a break in this safe surrounding, it is so short that there is no significant recontamination and there is no doubt about the clinical success when implanting such a stent.

The stent can advantageously, as described above, be compressed in a provision device. Then the stent is not subjected to the surrounding atmosphere or other contaminating substances during the compression, or only to an insignificant extent. Contaminating the stent surface during the crimping process can be avoided thereby.

In one variant of the method according to the invention, the stent can be provided in a packaging that serves as a storage space and has an inert filling. The packaging with the stent is inserted into the provision device with the crimping apparatus, i.e. it is inserted between the elements of the crimping apparatus, which can move in the radial direction for compressing the stent. Thus the stent need not be compressed in a cleanroom. The stent can be prepared for the implantation at the producer or else in situ in the normal premises of a hospital.

In another variant of the method, the crimping apparatus is at least in part stored within the storage space consisting of an inert medium or with an inert filling, or it is inserted therein and actuated from outside of the storage space. By way of example, if a container is provided as a storage space, the inert filling of which is provided by water or a gas that is heavier than air, the moveable elements of the crimping apparatus for example can be inserted into the container through an upper opening in the container. Hence the stent can remain in the inert envelope in the storage space and need not be removed from this protected surrounding to run through a crimping process.

A cleaning treatment, as mentioned above, can for example ablate material, namely e.g. by means of sputtering as ion bombardment, electric discharge machining, electrolytic polishing, plasma activation, laser ablation, mechanically abrasive methods, dry etching or wet-chemical etching. Alternatively, the surface treatment for reducing the chemical contamination results in an unchanged topography of the surface, wherein the treatment in this case can also be brought about by means of e.g. sputtering as ion bombardment, electric discharge machining, electrolytic polishing, plasma activation, laser ablation, mechanically abrasive methods, dry etching or wet-chemical etching. A treatment that does not ablate material, e.g. by means of ultrasound, UV light or ozone, or a combination treatment formed therefrom, can likewise lead to an unchanged surface topography. An etching medium that does not corrode the stent material itself is equally suitable for this.

Furthermore, it is advantageous that a cleaning treatment significantly also reduces contaminants from the surface of elements of the crimping apparatus that contact the stent in order to compress the stent. The same cleaning methods that were used for the stent can be utilized in this case. The elements of the crimping apparatus are particularly advantageously cleaned together with the stent.

In a preferred embodiment of the method according to the invention, the stent is arranged in a compressed fashion on or in a catheter in the inert storage space, and so the stent can be removed from the storage space without being subjected to recontamination in the process. To this end at least one distal end of a catheter is provided in the storage space. In the case of a balloon-expanding stent, the stent is compressed onto a balloon at the distal end of the catheter. In the case of a self-expanding stent, the stent is compressed by the crimping apparatus and subsequently inserted into the distal end of a tube catheter, or the tube catheter is pushed over the compressed stent. The stent can also be removed together with the catheter from the storage space with the aid of a transfer vessel, as explained above.

In the case of a self-expanding stent, the stent can also be cooled after the crimping process in order to promote the compressed state of the stent being maintained. This is expedient in the case of e.g. nickel-titanium stents. On the other hand, balloon-expanding stents can also be tempered during the compression in order to increase the adhesion to the balloon catheter. A suitable temperature depends on the material of the stent. A tempering apparatus is provided for this in the provision device.

In the method according to the invention, all steps for providing the stent for implantation into a body volume are carried out after the production thereof in a controlled environment. The stent is preferably inserted into the storage space after the surface has been cleaned, more particularly in order to generate a hydrophilic surface, or it is already located in the storage space during the cleaning, it is compressed in the storage space and it is subsequently arranged on or in the catheter. The catheter, or the distal end thereof with the stent, is removed from the storage space for implantation purposes and inserted into the body of the patient. The stent is only released at the treatment site within the body. Hence the stent is at least for most of the time situated in the controlled environment from the cleaning treatment onward and a renewed significant contamination can be excluded. As described above previously, the cleanliness of the stent is not adversely affected by short breaks in the inert envelope. By way of example, such breaks can occur during the transfer of the stent from the cleaning treatment into the provision device or from the provision device into a shipping packaging. Furthermore, such a break can also occur during a work step for providing the stent, e.g. during the compression, provided no significant recontamination occurs in the process.

Hence, in principle, the inert surroundings can also be changed between or during the work processes for providing the stent for implantation provided it can be ensured that there is no significant recontamination. By way of example, the stent can be stored in an inert fashion in a liquid medium while it is subjected to a cleaning treatment and it can subsequently be transferred from the liquid medium into a packaging with a gaseous inert filling. When it is removed from the liquid medium, a liquid film may remain on the surface of the stent and protect the latter from contaminants until it has been introduced into the new inert surroundings in the packaging. The stent with the packaging can be introduced into the provision device with the crimping apparatus and can be compressed therein.

BRIEF DESCRIPTION OF THE DRAWINGS

Preferred embodiments of the invention will be illustrated in the following text with the aid of the drawings, which merely serve for explanation and should not be construed as being restrictive. The features of the invention becoming obvious from the drawings should be considered to be part of the disclosure of the invention both on their own and in any combination. In the drawings:

FIG. 1A shows a balloon-expanding or self-expanding stent in an uncrimped state;

FIG. 1B shows a storage space in the form of a packaging with a stent as per FIG. 1A stored therein in an inert filling;

FIG. 2A shows a device according to the invention with access into a storage space and an open crimping apparatus integrated therein;

FIG. 5A shows a device according to the invention according to a second embodiment with a self-expanding stent, a catheter, and a crimping apparatus, in an opened state, arranged within the storage space;

FIG. 5C shows a device according to the invention according to the second embodiment with the stent in the compressed state and an opened crimping apparatus;

FIG. 6 shows a storage space with a self-expanding stent stored therein in an inert filling, mounted on a catheter and in the crimped state;

FIG. 8A shows a device according to the invention according to a fourth embodiment with a self-expanding stent and a crimping apparatus, in an opened state, arranged outside of the storage space;

FIG. 8B shows a device according to the invention according to the fourth embodiment with the crimping apparatus in a closed state;

FIG. 8C shows a device according to the invention according to the fourth embodiment with the crimping apparatus in an opened state and the stent in a compressed state;

DETAILED DESCRIPTION OF THE EMBODIMENTS

Figure 2C:
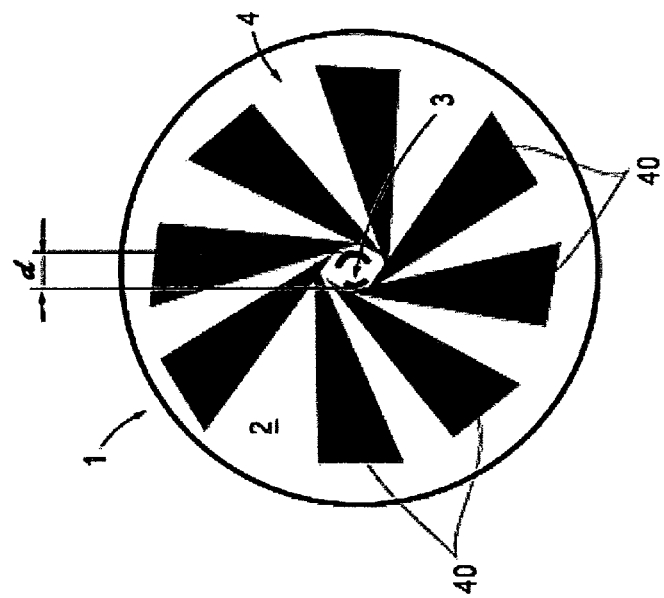
FIG. 2C shows the crimping apparatus from FIG. 2A in the closed state.

In the illustrated exemplary embodiments, the same components are labeled by the same reference sign. The following statement holds true for the entire subsequent description: If reference signs are contained in a figure for the purpose of unambiguity in the drawing but not mentioned in the directly associated text of the description, reference is made to the description thereof in the preceding or subsequent description of the figures. In the interest of clarity, repeated designation of components in further figures is generally dispensed with, provided it is clear from the drawing that these are "recurrent" components.

FIG. 1A:

The illustrated stent 3 has a conventional material configuration and structural design; it could be balloon-expanding or self-expanding. The stent 3 is of length 1, which extends between the proximal end 31 and the distal end 32. In the non-crimped state, the stent 3 assumes the diameter d, and so the webs 33 with the surface 35 are spaced from one another in a spacious and grid-shaped fashion. The stent lumen 34, in principle of cylindrical design, runs through the tubular stent 3. The stent 3 may have a coating, more particularly a coating with active substances that should be introduced into the body of a patient.

FIG. 1B:

The stent 3 is in a storage space in the form of a packaging 1, which can be inserted into a provision device according to the invention. Here the stent 3 is fixed by a support 13 arranged in the packaging 1, which support first of all comprises a first support element 131, which stands against the proximal end 31. The distal end 32 is held by the second support element 132. The packaging 1 first of all comprises the container 12 with the base 10 and is sealed by the cover 11 on the end opposite the base 10. Container 12, base 10 and cover 11 can have an integral design; at least the cover 11 can preferably be removed or it can be folded back or opened in order to open the container 12. The first support element 131 extends like a separation wall over the cross-sectional area of the container 12 and faces the cover 11, wherein a third support element 133 connects the cover 11 with the first support element 131 in the axial direction. The second support element 132 likewise extends like a separation wall over the cross-sectional area of the container 12, but it faces the base 10. There is an inert filling 2 in the storage space 1 and it protects the surface 35 of the stent 3. The inner faces of the storage space 1 facing the stent 3 are inert.

The preceding treatment of the surface 35 increased the hydrophilic property thereof. The molecular-chemical contaminants on the surface 35 originating from the atmosphere—mainly hydrocarbons—were reduced significantly, as a result of which, as a measure of the hydrophilicity, the contact angle of a water droplet situated on the surface 35 is reduced.

The chemical contaminants on the surface 35 can be reduced by material ablation. Sputtering as ion bombardment, electric discharge machining, electrolytic polishing, plasma activation, laser ablation, mechanically abrasive methods, dry etching or wet-chemical etching lends itself for this purpose. Alternatively, the reduction in the chemical contaminants on the surface 35 is achieved by a treatment that does not change the topography of the surface 35. Treatment by means of ultrasound, UV light, ozone, or a combination treatment formed therefrom, can be considered for this. An etching medium that does not corrode the stent material itself is equally suitable for the treatment, for example an acid treatment of the surface. 95%-97% sulfuric acid on cobalt-chromium alloys and on nickel-titanium alloys have proven their worth.

The surface treatment may also be carried out within the storage space in the form of the packaging 1. In this case a cleaning method that does not ablate material is preferred.

Figure 2B:
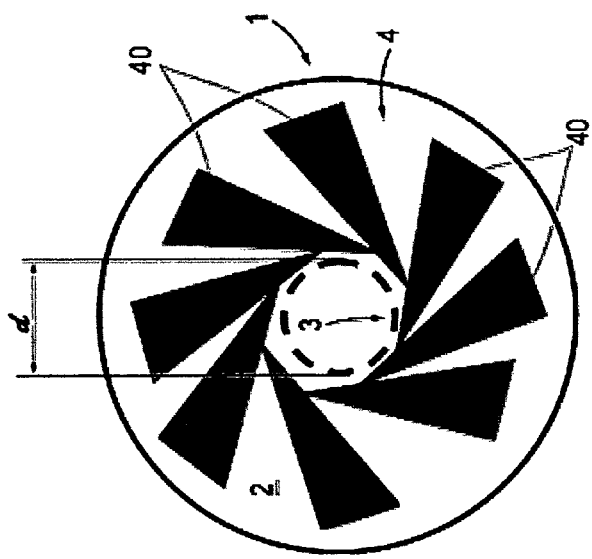
FIG. 2B shows the crimping apparatus from FIG. 2A in the open state.

FIGS. 2A to 2C:

This group of figures schematically illustrates the function of a device for providing a stent for implantation into a body lumen according to the present invention. The device comprises the storage space in the form of the packaging 1, a crimping apparatus 4 with crimping elements in the form of jaws 40 and an activator 42 for actuating the crimping apparatus. The stent 3 and the jaws 40 of the crimping apparatus 4 are stored in an inert filling 2 in the storage space in the form of the packaging 1. At first, the crimping apparatus 4 is open, and so the jaws 40 thereof assume a dilated position and encompass the expanded stent 3 situated in the packaging 1 (see FIGS. 2A, 2B). The stent 3 is pretreated as already explained with reference to FIG. 1B. The packaging 1 in turn contains the inert filling 2 and the inner wall of the packaging is inert. The jaws 40 are seated on a shaft 41, which, in the axial direction, leads outward through a passage 100 in the storage space to an actuatable activator 42. Axes 15, which extend axially between the base 10 and the cover 11, pass through the container 12. A guide mandrel 43 belonging to the crimping apparatus 4 runs centrally through the container 12, which mandrel ends within the container 12 in front of an access 110, which is on the storage space and can be perforated. If the crimping apparatus is closed, the jaws 40 are narrowed in the radial direction, and so the stent 3 has a compressed diameter d (see FIG. 2C).

Figure 3A:
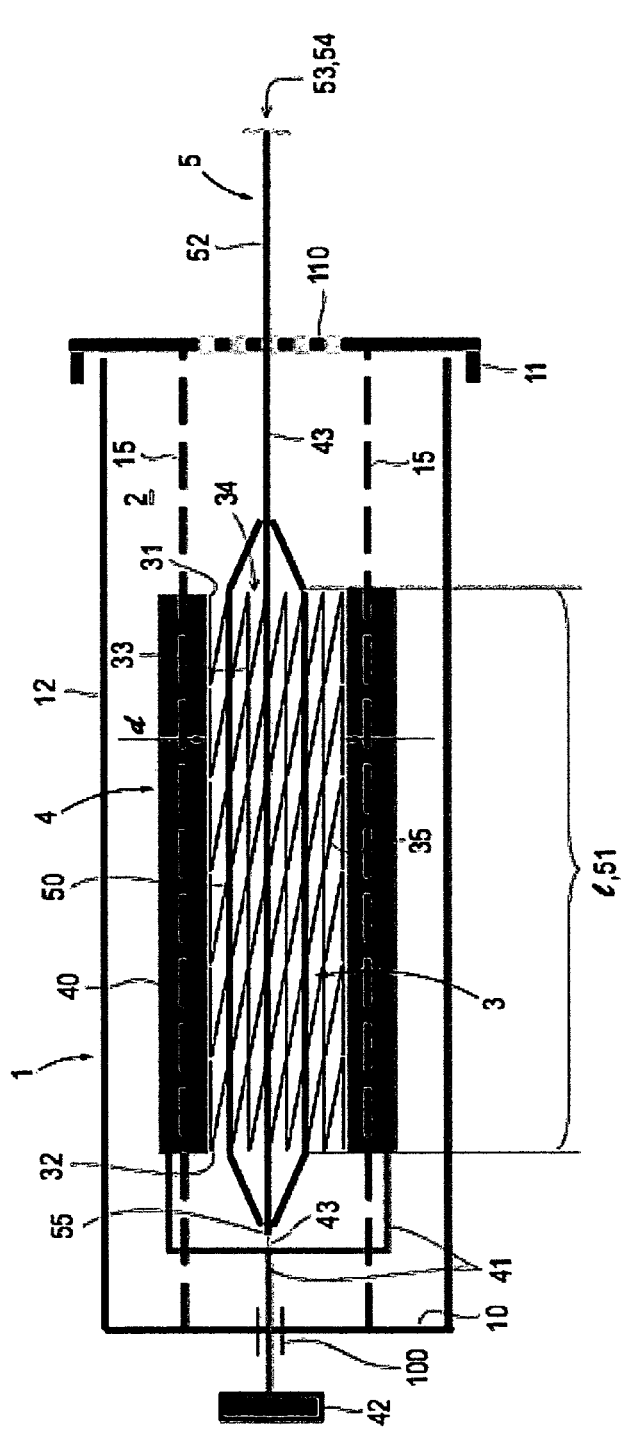
FIG. 3A shows a device according to the invention according to a first embodiment with a balloon-expanding stent and a crimping apparatus, in an opened state, arranged within the storage space.
Figure 3B:
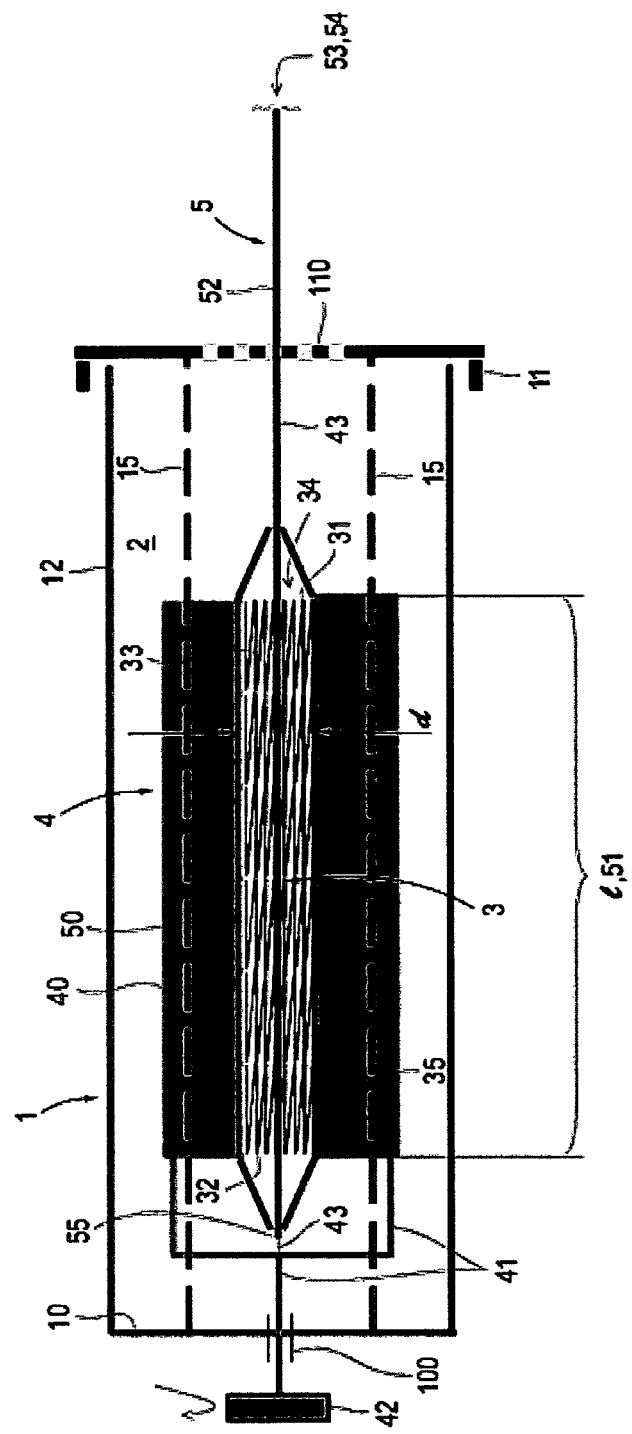
FIG. 3B shows a device according to the invention according to the first embodiment with the crimping apparatus in a closed state.

FIGS. 3A and 3B:

This pair of figures shows a first embodiment of a device according to the present invention with a balloon-expanding stent and a crimping apparatus arranged within the storage space. The stent 3 was subjected to pretreatment in order to increase the hydrophilicity of the surface 35, as explained with reference to FIG. 1B. Once again, an inert filling in the storage space in the form of the packaging 1 and an inert property of the inner wall thereof are assumed. The jaws 40 of the crimping apparatus 4 are open at first (see FIG. 3A). The balloon 50 of the catheter 5 arranged on the shaft 52 has been inserted into the stent lumen 34, tip 55 first, through the access 110, which is in the storage space and can be perforated. In the process, the guide mandrel 43 has penetrated the guide wire lumen 53 in the shaft 52. The shaft 52 furthermore has the channel-like dilation lumen 54, by means of which the balloon 50 can be brought to expand by being filled up on the inside—e.g. by means of physiological saline—from an external source during the operation and thus dilates the stent 3 from the inside. The stent region 51 of the balloon 50 is in the stent lumen 34, and so the stent region 51 at least in principle passes through the entire length 1 of the stent, while the tapering ends of the balloon 50 protrude from the proximal end 31 and the distal end 32 of the stent 3.

After actuating the activator 42 by rotating it, e.g. manually, the crimping apparatus 4 reaches the closed state, and so the diameter d of the stent 3 is pressed together (see FIG. 3B). In the case of the now narrowed stent diameter d and the compressed jaws 40 of the crimping apparatus 4, the stent region 51 of the balloon 50 remains in an unchanged axial position within the stent lumen 34.

Figure 4:
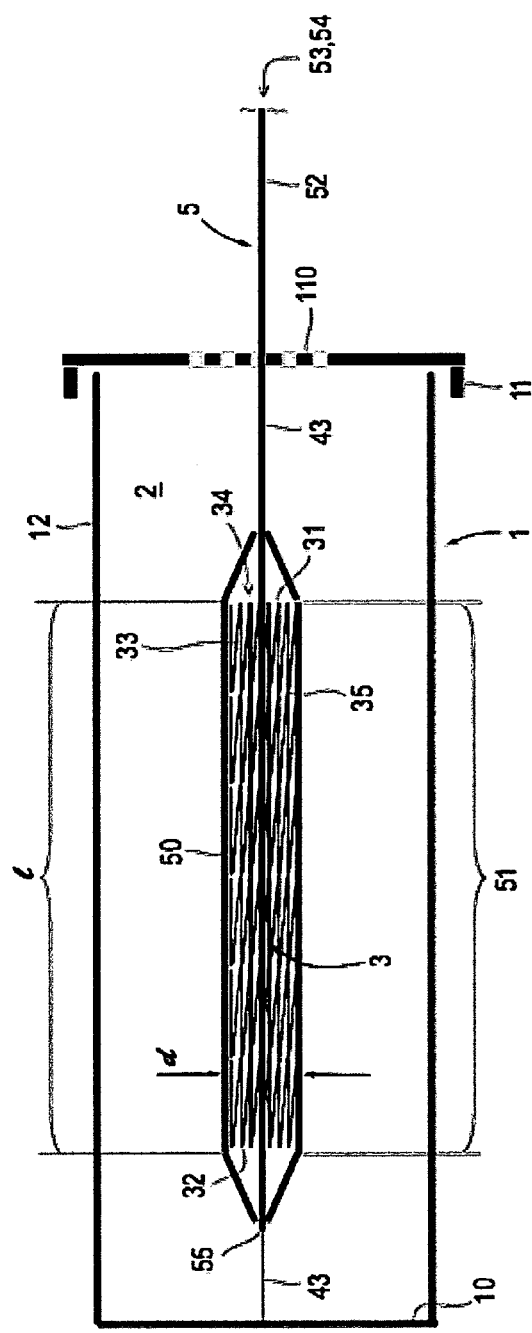
FIG. 4 shows a packaging with a balloon-expanding stent stored therein in an inert filling, on a dilation catheter in the crimped state.

FIG. 4:

FIG. 4 shows the packaging 1 from which the crimping apparatus 4 was removed or from which the storage space was taken out of the provision device. The balloon-expanding stent 3 can now be kept in the packaging 1 on the balloon 50 of a dilation catheter 5 in the crimped state. Here, the stent diameter d is narrowed and the webs 33 are pushed against one another. The stent region 51 of the balloon 50 once again extends over the length 1 of the stent, at least in principle. The guide mandrel 43, which extends from the base 10, has penetrated the guide wire lumen 53 of the shaft 52. The tip 55 comes to rest near the base 10. The interior of the packaging 1 is provided with the inert filling 2 that protects the surface 35 of the stent 3, which is pretreated as per the description in respect of FIG. 1B. Furthermore, the assumption is made that the inner wall of the packaging 1 is inert. The dilation catheter including crimped stent 3 and balloon 50 can be pulled out of the packaging 1 through the access 110, which is in the storage space and can be perforated. When the storage space with the stent 3 is inserted into the provision device in order to compress the stent, the elements of the crimping apparatus for example can also be inserted into the storage space through the access 110. The elements of the crimping apparatus can alternatively also be introduced into the storage space by removing the cover or the base and inserting the elements into the packaging.

FIGS. 5A to 5E:

FIGS. 5A to 5E show a second embodiment of a device for providing a stent 3 for implantation into a body lumen, with a self-expanding stent and the crimping elements in the form of jaws 40 of the crimping apparatus 4 being arranged in the storage space thereof in the form of the packaging 1. The distal end of a tube catheter 6 is inserted into the storage space. The crimping apparatus 4 once again includes the shaft 41, which extends to the activator 42 through the passage 100 in the base 10, and the guide mandrel 43 passing axially through the packaging 1. The packaging 1 contains the inert filling 2 and the packaging inner wall is inert. The axes 15 again lie within the packaging 1. The surface 35 of the stent 3 has been pretreated in order to increase the hydrophilicity, as explained with reference to FIG. 1B.

FIG. 5A (Initial Situation):

The jaws 40 of the crimping apparatus 4 are open; it follows that the stent 3 is in the uncrimped state and the inner tubing 66 of the tube catheter 6 has been pushed through the access 110, which is in the cover 11 of the storage space and can be perforated, and through the stent lumen 34 to the extent that the tip 65 protrudes from the stent 3 and faces the base 10. The guide mandrel 43 has penetrated the guide wire lumen 63 of the shaft 62 in the axial direction. The support tubing 67 and the outer tubing 68 have likewise been pushed through the access 110, which can be perforated, but the free ends thereof are in front of the proximal end 31 of the stent 3. The stent region 61, which can hold the length 1 of the stent, extends between the free end of the support tubing 67 and the stop 69 at the tip 65.

Figure 5B:
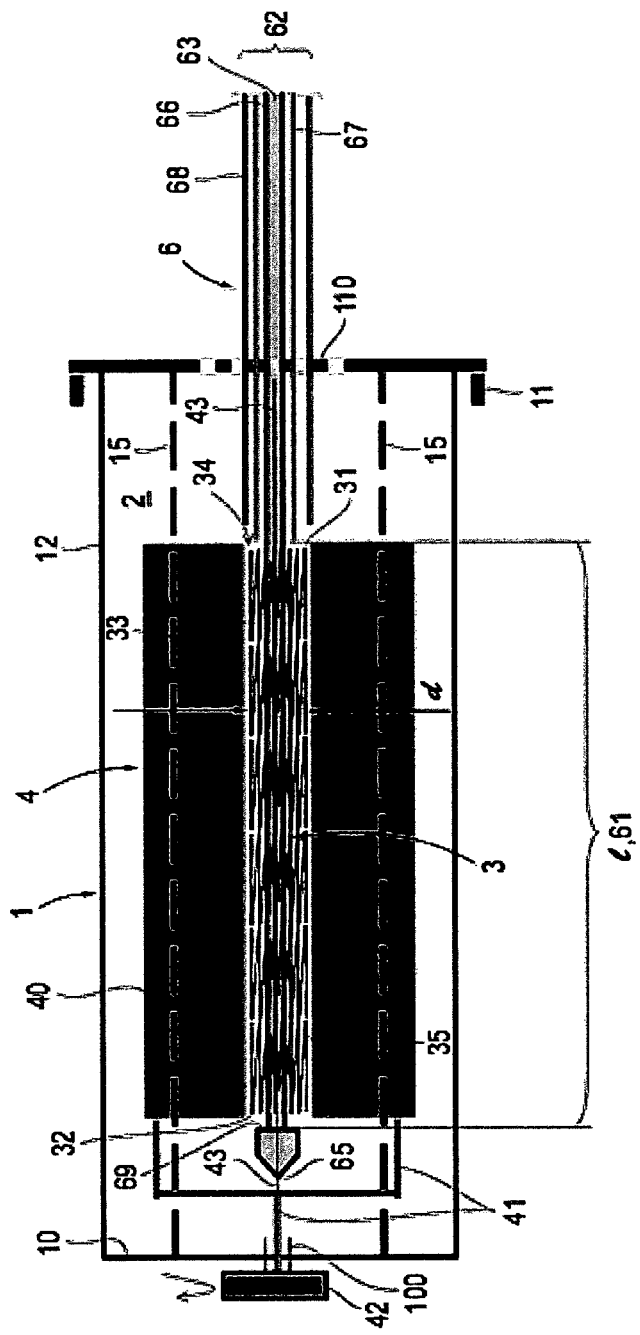
FIG. 5B shows a device according to the invention according to the second embodiment with the crimping apparatus in a closed state.

FIG. 5B (1st Continuation Step):

The jaws 40 of the crimping apparatus 4 have now been closed, and so the webs 33 of the stent 3 lie pushed together and the stent diameter d is narrowed. The crimping apparatus 4 was actuated by rotating the activator 42, which is arranged outside of the storage space. The tube catheter 6, comprising the tip 65, the inner tubing 66, the support tubing 67, and the outer tubing 68, remains in the same position. The stent 3 can be cooled in the crimped state in order to disable the self-expanding property when the temperature drops below a defined threshold. By way of example, a cooling spray or cooling elements, such as Peltier elements, can be used for the cooling. When selecting the inert medium or the inert filling, care has to be taken that the medium or the filling does not change its state, e.g. freezes, as a result of the cooling.

FIG. 5C (2nd Continuation Step):

The jaws 40 of the crimping apparatus 4 are opened, with the self-expanding stent 3 remaining in the crimped state with the narrowed stent diameter d and the compacted webs 33 as a result of the prior temperature drop.

Figure 5D:
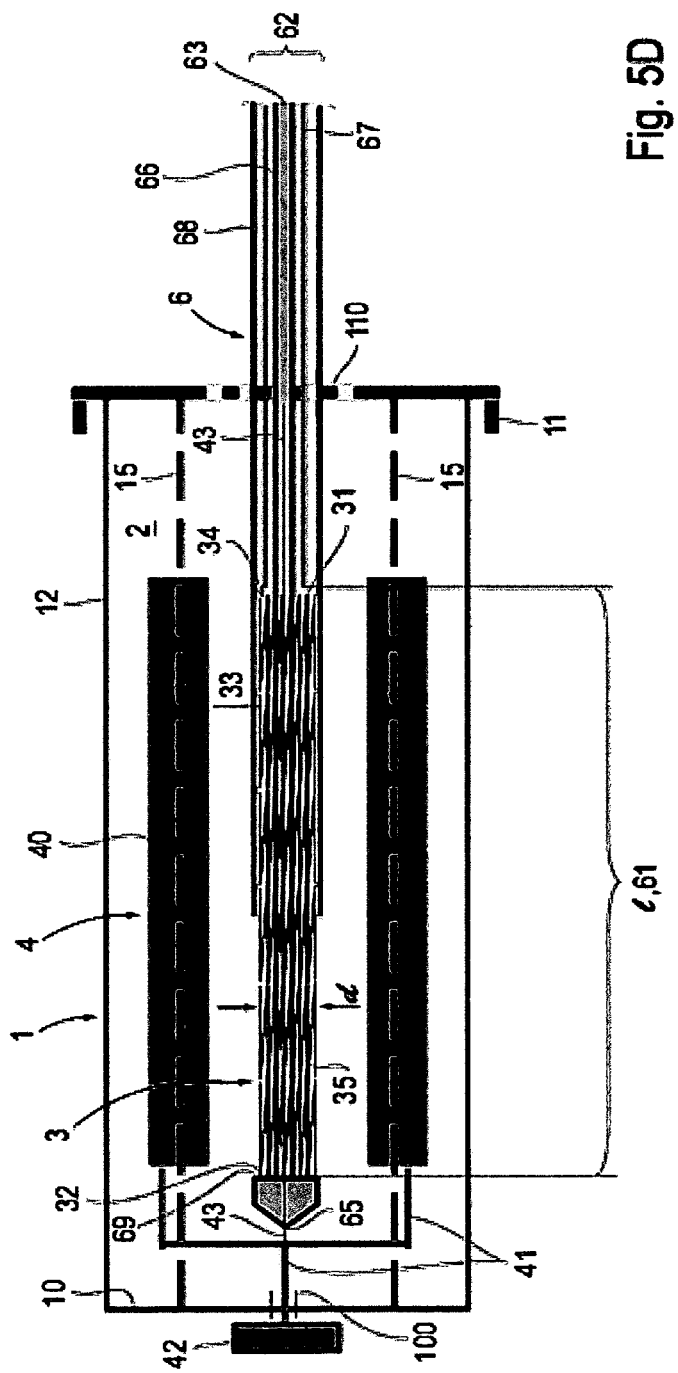
FIG. 5D shows a device according to the invention according to the second embodiment with an outer tubing of the catheter that has in part been pushed over the crimped stent.

FIG. 5D (3rd Continuation Step):

The stent 3 remaining in the crimped state with the narrowed stent diameter d allows successive pushing of the outer tubing 68 onto the stent 3 in the direction of the distal end 32 from the proximal end 31. The support tubing 67 and the tip 65 arranged on the inner tubing 66 remain in the same position. The advance of the outer tubing 68 also moves the stent 3 in the same direction, with the stop 69 preventing the further advance of the stent 3.

Figure 5E:
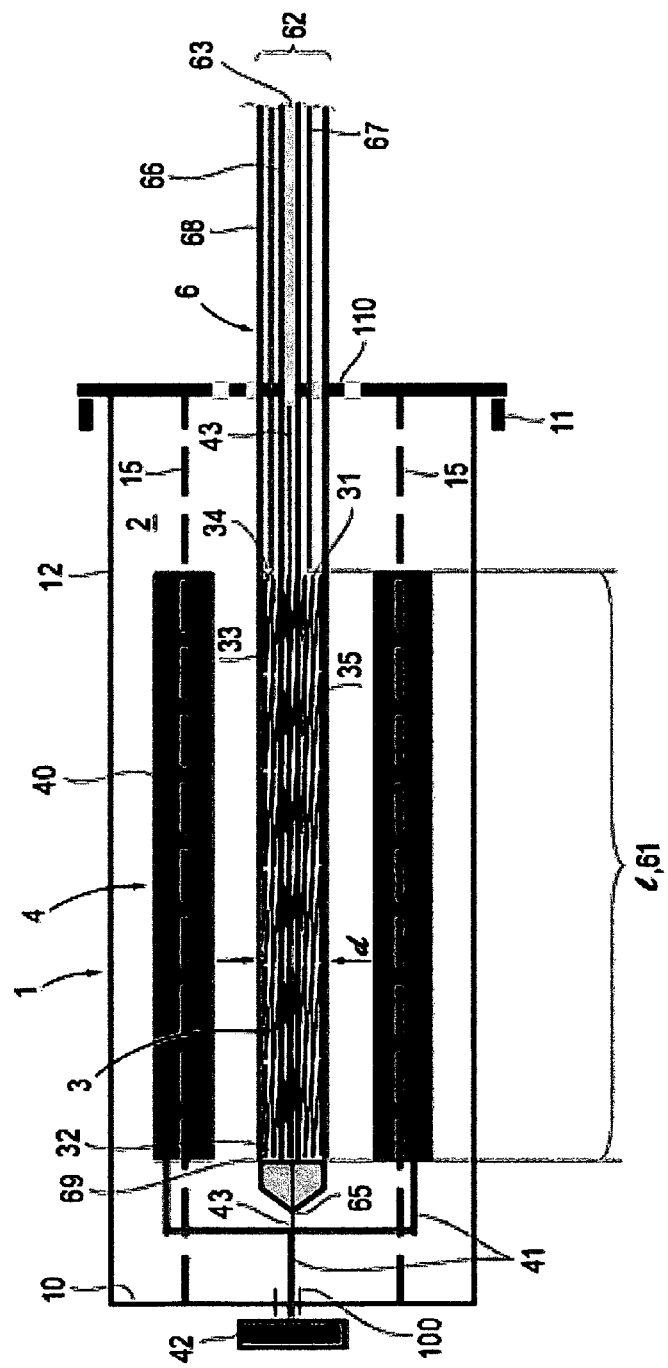
FIG. 5E shows a device according to the invention according to the second embodiment with an outer tubing of the catheter completely pushed over the crimped stent.

FIG. 5E (4th Continuation Step):

The outer tubing 68 has been pushed so far over the crimped stent 3 that it meets the stop 69 behind the tip 65 and it follows that it now covers the entire stent region 61. During the work steps of compressing and accommodating in the catheter, the stent 3 is stored in the inert filling 2 in the storage space of the provision device such that there cannot be any undesired contamination during the transfer from the crimping apparatus to the catheter. In order to implant the stent, the tube catheter 6 with the crimped stent 3 accommodated therein is pulled out of the packaging 1 through the access 110, which can be perforated, in order to apply the stent 3, which has been prepared as detailed above, to the patient at the predetermined site in the body.

FIG. 6:

In principle, the jaws 40 can be removed from the storage space and the stent can be stored in the storage space such that the latter serves as a packaging for the stent. The guide mandrel 43 has been inserted into the guide wire lumen 63. The shaft 62 with outer tubing 68, support tubing 67 and inner tubing 66 protrude outward through the access 110, which is in the storage space and can be perforated. The outer tubing 68 butts against the stop 69 of the tip 65 and thus spreads over the entire region 61 of the stent. The free end of the support tubing 67 is in front of the proximal end 31 of the stent 3. Further handling is brought about as in connection with FIG. 5E.

Figure 7A:
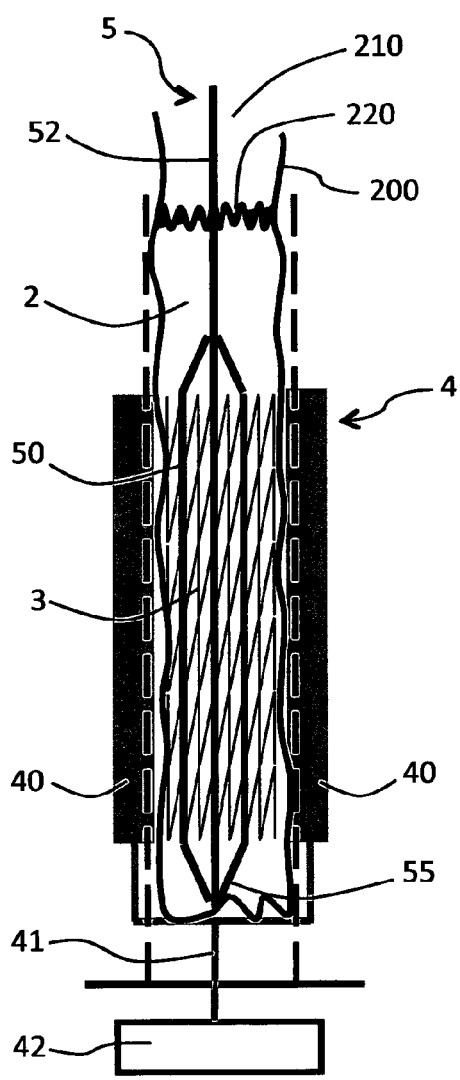
FIG. 7A shows a device according to the invention according to a third embodiment with a balloon-expanding stent and a crimping apparatus, in an opened state, arranged outside of the storage space.
Figure 7B:
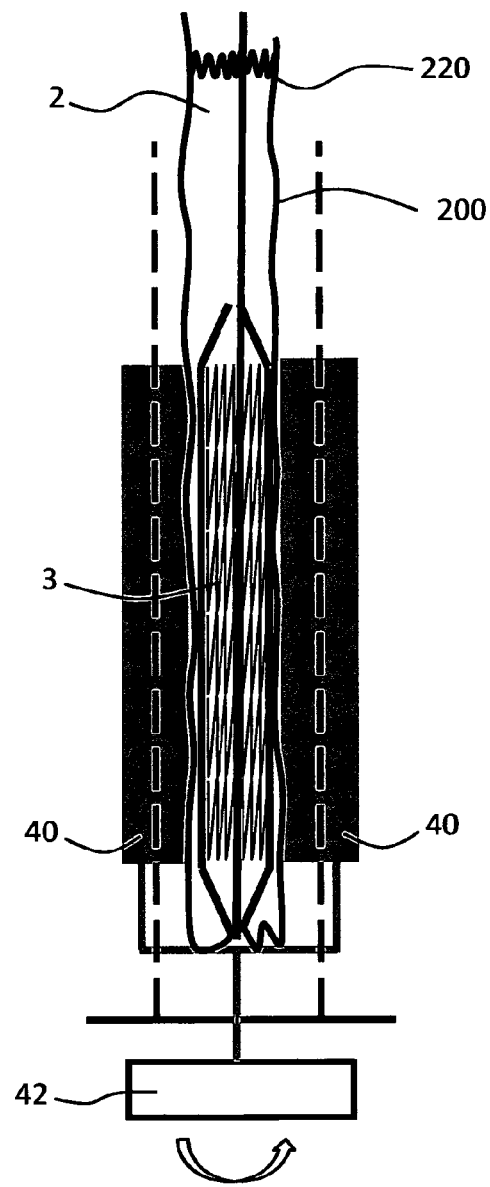
FIG. 7B shows a device according to the invention according to the third embodiment with the crimping apparatus in a closed state.

FIGS. 7A and 7B:

FIGS. 7A and 7B show a third embodiment of a provision device according to the present invention, in which the crimping apparatus 4 is arranged completely outside of a storage space 200. The storage space 200 is designed as tubing that is closed at one end, which tubing can be compressed laterally such that the diameter of the tubing can be reduced. At the opposite end, the tubing has an opening 210. The tubing can be made of an inert material or merely have an inert inner surface. The interior of the tubing 200 is filled with an inert liquid medium 2. Care has to be taken that the filling level of the medium 2 in the dilated state of the tubing is selected such that the medium 2 does not escape from the tubing in the compressed state of the tubing either, in which there is a reduced interior volume compared to the dilated state. A balloon-expanding stent 3 and an associated balloon catheter 5, as explained in detail with reference to FIGS. 3A and 3B, are provided in the storage space 200. The filling level 220 of the inert medium 2 in the tubing 200 is so high that said medium completely surrounds the stent 3 and the balloon 50 for at least most of the time, and so the stent is stored in an inert fashion in the storage space.

The crimping apparatus 4 comprises the jaws 40 and the shaft 41. An activator 42 is used to activate the crimping apparatus 4. The opening of the crimping apparatus between the crimping elements of the provision device is arranged in a vertical fashion, and so the tubing 200 can be inserted into the crimping apparatus 4 of the provision device in a vertical fashion with the opening 210 facing upward and the jaws 40 encompass the stent 3. In principle, a horizontal arrangement of the crimping elements and the stent introduced therein can also be selected, provided the opening 210 faces upward and it is ensured that the inert filling does not escape from the tubing while the stent is being compressed and hence the volume of the tubing is being reduced.

In FIG. 7A, the stent, which is in an uncompressed state, was inserted into the crimping apparatus by means of the tubing 200 with the opening 210 facing upward. Here the stent 3 is stored in the inert filling 2 and protected from recontamination.

FIG. 7B shows the crimping apparatus 4 with narrowed jaws 40, and so the storage space and the stent in the storage space are compressed. The activator 42 was actuated, e.g. rotated, to this end in order to move the jaws 40 toward the inside into the free space around the axis of the crimping apparatus 4, and so they engage on the external circumference of the stent and compress the latter toward the axis. In the process, the stent is pressed onto the balloon, as described with reference to FIGS. 3A and 3B. The filling level 220 of the inert medium 2 in the tubing rises as a result of compressing the tubing.

The jaws 40 can be reopened after the crimping process by means of the activator 42 and the tubing storage space 200 can be removed from the provision device. The filling level 220 falls back to its original value. The stent 3 and the balloon 50 of the catheter 5 remain stored within the inert medium over the entire procedure, starting from the insertion of the storage space into the provision device, over the crimping procedure and through to the removal from the provision device. The tubing can be sealed at the opening 210 after it has been removed from the provision device, and so the tubing can serve as transportation packaging.

FIGS. 8A to 8C:

FIGS. 8A to 8C show a fourth embodiment of a provision device according to the present invention, in which the crimping apparatus 4 is likewise arranged completely outside of a storage space 200. The storage space 200 is designed as tubing and filled with an inert medium 2, analogously to the embodiment according to FIGS. 7A and 7B. A self-expanding stent 3 is stored in the tubing and the distal end of a tube catheter 6 is inserted through the opening 210. The tube catheter has a design substantially corresponding to the embodiment according to FIGS. 5A to 5E. The catheter is inserted so far into the storage space, i.e. the tubing 200, that the ends of the outer tubing 68 and the support tubing 67 protrude into the inert medium 2, to be precise both in the case of a filling level 220 when the jaws 40 are open and when the jaws 40 of the crimping apparatus 4 are closed.

The crimping apparatus is aligned vertically in the provision device and actuated by the activator 42.

FIG. 8A shows the provision device with opened jaws 40 of the crimping apparatus 4, wherein the stent is encompassed by the jaws 40. In FIG. 8B, the activator 42 was actuated such that the jaws 40 act on the stent 3 and compress the latter. The stent can now be cooled, e.g. by cooling the inert medium or in another fashion, in order to disable the self-expanding property, as described with reference to FIG. 5B. The crimping apparatus can subsequently be opened, as shown in FIG. 8C. The outer tubing 68 can be pushed over the stent, as explained with reference to FIGS. 5D and 5E, wherein the stent is in turn accommodated between the stop 69 and the support tubing 67. As soon as the outer tubing 68 covers the entire region 61 of the stent and butts against the stop 69, the stent is stored in an inert fashion within the catheter and can be removed from the tubing 200 without renewed contamination being possible. However, the stent and the catheter can also be removed from the provision device together with the tubing 200, and so the tubing 200 can again serve as transportation packaging after the opening 210 is sealed.

Figure 9A:
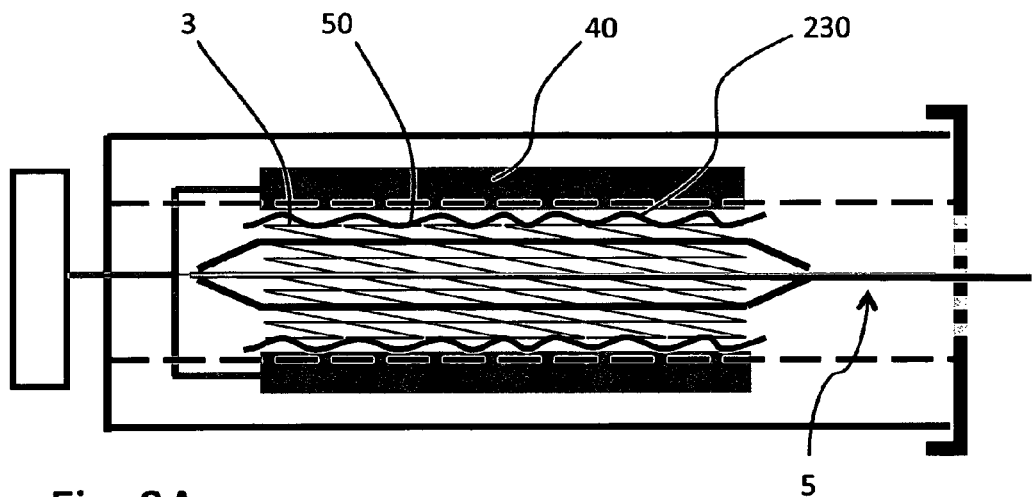
FIG. 9A shows a device according to the invention according to a fifth embodiment with a protective sheath, a balloon-expanding stent and an opened crimping apparatus.
Figure 9B:
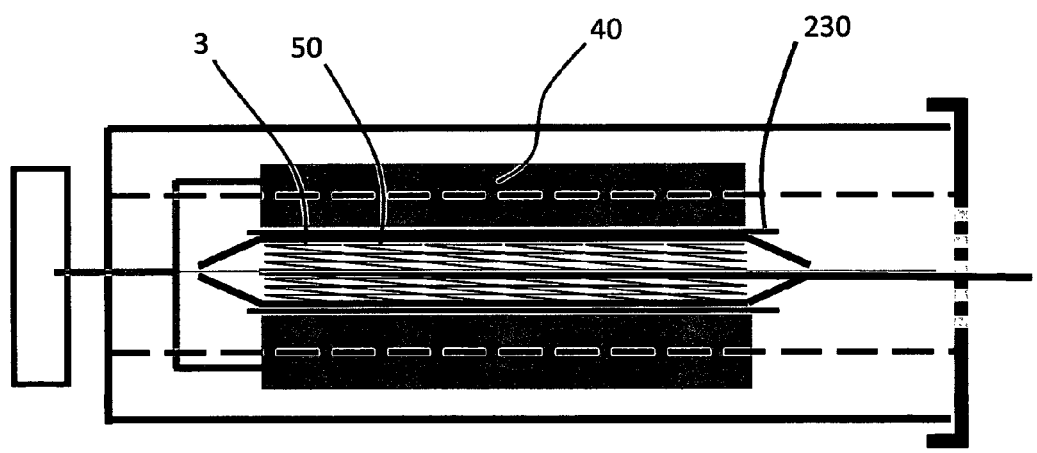
FIG. 9B shows a device according to the invention according to the fifth embodiment with a closed crimping apparatus.

FIGS. 9A and 9B:

FIGS. 9A and 9B show a provision device according to a fifth embodiment according to the invention. The provision device substantially corresponds to that of FIGS. 3A and 3B, in which the crimping jaws 40 of the crimping apparatus 4 are within the storage space and hence within the inert filling 2. A protective sheath 230, which surrounds the stent 3, is provided between the jaws 40 and the stent 3 over the entire length l of the stent. Hence the jaws 40 do not come to rest directly on the surface 35 of the stent when the stent is being compressed. The protective sheath 230 can be inserted together with the stent during the introduction thereof into the storage space. However, it can also be fixedly attached to the elements of the crimping apparatus or be arranged thereon in a replaceable fashion.

FIG. 9A shows the provision device with an opened crimping apparatus 4, with the stent being in an expanded state. The crimping apparatus 4 is closed in FIG. 9B and the stent was crimped onto the balloon 50.

Figure 10:
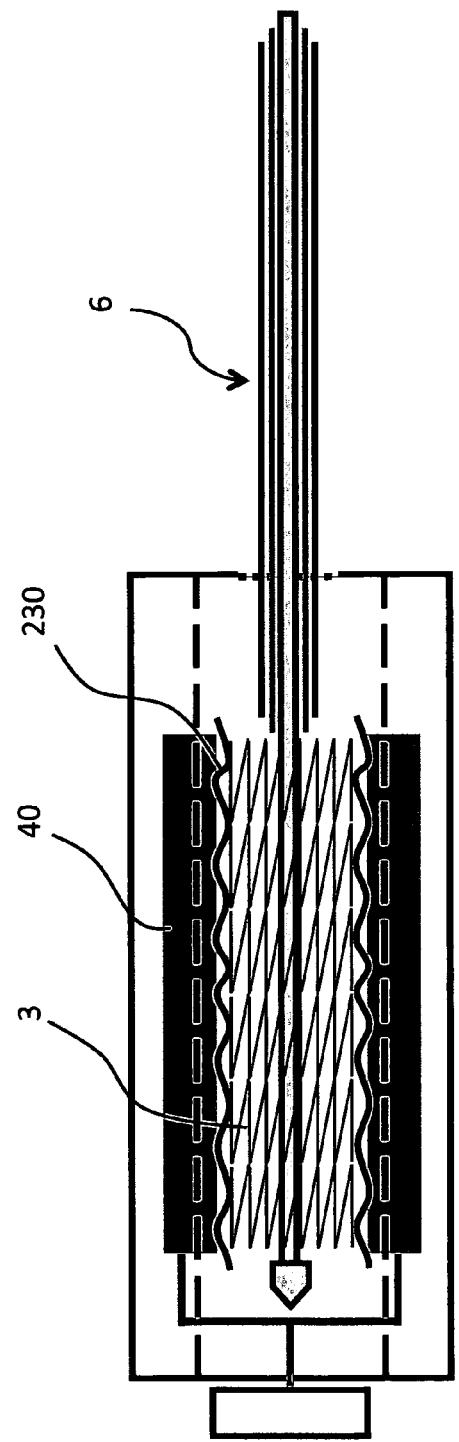
FIG. 10 shows a device according to the invention according to the fifth embodiment with a self-expanding stent.

FIG. 10:

FIG. 10 shows a provision device according to the fifth embodiment using a self-expanding stent 3 and a tube catheter 6, in which a protective sheath 230 once again surrounds the stent 3. The stent is compressed analogously to the procedure described with reference to FIGS. 5A to 5E. As soon as the jaws 40 are reopened after the crimping procedure, the protective film 230 also re-dilates to the extent that the outer tubing 68 can be pushed through between the protective sheath 230 and the stent surface 35 until the stent is accommodated in the catheter. Here the protective sheath 230 remains outside of the catheter.

In the illustrated embodiments, use is made of a crimping apparatus with jaw elements that act on the stent for the purpose of compression. However, in principle other crimping apparatuses are also suitable for use in the provision device according to the invention, e.g. as illustrated in the description relating to the prior art.

In order to carry out the method according to the invention, the stent may also be completely removed from its inert envelope and supplied to a crimping apparatus, which compresses the stent outside of the inert envelope, provided the period of time during which the stent is not protected by the inert envelope does not permit significant recontamination. A provision device according to the invention in principle also allows such a process.

LIST OF REFERENCE SIGNS

1 Storage space
2 Filling
3 Stent
4 Crimping apparatus
5 Balloon catheter
6 Tube catheter
10 Base
11 Cover
12 Container
13 Support
15 Axis
31 Proximal end
32 Distal end
33 Webs
34 Stent lumen
35 Surface
40 Jaws
41 Shaft
42 Activator
43 Guide mandrel
50 Balloon
51 Region of the stent
52 Shaft
53 Guide wire lumen
54 Dilation lumen
55 Tip
61 Region of the stent
62 Shaft
63 Guide wire lumen
65 Tip
66 Inner tubing
67 Support tubing
68 Outer tubing
69 Stop
200 Storage space
210 Opening
220 Filling level
230 Protective sheath
l Length of the stent
d Stent diameter

What is claimed is:

1. A device for providing a stent for implantation into a body lumen, wherein the stent is hydrophilized and has a proximal end and a distal end, with a stent lumen with a compressible diameter extending therebetween, the device comprising:

a crimping apparatus with crimping elements which are arranged around an axis and movable radially with respect to the axis relative to one another, and an activator for actuating the crimping apparatus, wherein the crimping elements encompass the stent and are movable in the radial direction from a dilated position, in which the stent is uncrimped, into a closed position, in which the stent has a compressed diameter, by the activator, and the device further comprising an inert medium in a storage space, configured for receiving the stent, and which forms an envelope configured for storing the stent is stored in an inert fashion while the crimping elements encompass the stent and are movable from the dilated position into the closed position.

2. The device as claimed in claim 1, wherein the crimping apparatus is arranged outside of the storage space of the stent.

3. The device as claimed in claim 1, further comprising a packaging, configured for storing the stent in an inert fashion in the inert medium, provided as the storage space.

4. The device as claimed in claim 3, wherein the packaging has a malleable wall.

5. The device as claimed in claim 3, wherein an access is provided for feeding the packaging with the stent between the elements of the crimping apparatus.

6. The device as claimed in claim 1, wherein the storage space is provided by a container, which is filled with an inert filling that is heavier than air.

7. The device as claimed in claim 1, wherein the stent is for stored in an inert fashion so as to permit a break in the inert envelope over a period of time during which there is no significant recontamination of the stent surface.

8. The device as claimed in claim 1, wherein at least a distal end of a catheter is provided within the storage space in order to hold the stent in the compressed state, wherein a balloon catheter or a tube catheter is assigned in a complementary fashion to a balloon-expanding or a self-expanding stent.

9. The device as claimed in claim 8, wherein the proximal end of the catheter protrudes out of the storage space through an access.

10. A method for providing a stent for implantation into a body lumen, wherein the stent is hydrophilized and has a proximal end and a distal end, with a stent lumen with a compressible diameter extending therebetween, comprising:

storing the stent in a storage space including an inert medium, configured for receiving the stent, which forms an envelope for the stent, and compressing the stent using a crimping apparatus with moveable crimping elements, which encompass the stent and are moved from a dilated position into a closed position, wherein the stent remains in the inert envelope or a break in the inert envelope is provided over a period of time during which there is no significant contamination of a surface of the stent or no significant increase in a contact angle of a water droplet on the surface of the stent.

11. The method as claimed in claim 10, wherein the inert envelope is broken during the compression of the stent.

12. The device method as claimed in claim 1, wherein the period during which the inert envelope is broken does not exceed approximately 15 minutes.

13. The method as claimed in claim 10, further comprising storing the stent in a packaging with an inert filling after the compression.

14. The method as claimed in claim 10, further comprising sterilizing the stent after the compression.

15. The method as claimed in claim 10, wherein the storage space is provided by a packaging configured for storing the stent, which packaging is inserted into the crimping apparatus.

16. The method as claimed in claim 10, further comprising storing the stent in a first inert medium or a first inert filling before the break in the inert envelope, and in a second inert medium or a second inert filling after the break in the inert envelope.

17. The method as claimed in claim 10, further comprising arranging the stent at a distal end of a catheter during the inert storage, wherein the stent is compressed onto a balloon at the distal end of the catheter in the case of a balloon-expanding stent, and wherein the stent is compressed by the crimping apparatus and subsequently inserted into the distal end of a tube catheter in the case of a self-expanding stent.

18. The method as claimed in claim 10, further comprising performing a cleaning treatment before or during the storing step, as a result of which, as a measure of hydrophilicity, the contact angle of a water droplet situated on the surface is reduced compared to the contact angle before the treatment.

19. The method as claimed in claim 18, wherein the molecular-chemical contaminants originating from the atmosphere, mainly hydrocarbons, are significantly reduced on the surface of the stent during the cleaning treatment.

20. The method as claimed in claim 18, wherein during the progression of the method steps of the cleaning treatment, the storage, the compression, the packaging and optionally the sterilizing, the stent remains in the inert envelope or provision is made for a break in the inert envelope over a period of time during which there is no significant contamination on a surface of the stent or no significant increase in a contact angle of a water droplet on the surface of the stent.

\* \* \* \* \*